US00PP16560P3

(12) United States Plant Patent
Delabroye

(10) Patent No.: US PP16,560 P3
(45) Date of Patent: May 23, 2006

(54) ***HEUCHERA* PLANT NAMED 'CARAMEL'**

(50) Latin Name: *Heuchera villosa*
Varietal Denomination: Caramel

(76) Inventor: Sandrine Delabroye, Rue Roger Salengro 40, Hantay (FR), F-59496

( * ) Notice: Subject to any disclaimer, the term of this patent is extended or adjusted under 35 U.S.C. 154(b) by 375 days.

(21) Appl. No.: 10/935,969

(22) Filed: Sep. 7, 2004

(65) Prior Publication Data

US 2006/0053519 P1 Mar. 9, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
(74) *Attorney, Agent, or Firm*—Penny J. Aguirre

(57) ABSTRACT

A new cultivar of *Heuchera villosa*, 'Caramel', characterized by its uniquely colored foliage of cordate-shaped leaves that emerge greyed-orange and mature to golden yellow-green, its vigorous growth habit and its resistance to disease.

2 Drawing Sheets

Botanical classification: *Heuchera villosa.*
Cultivar designation: 'Caramel'.

BACKGROUND OF THE INVENTION

The present invention relates to a new and distinct cultivar of *Heuchera villosa*, and is hereinafter referred to by the cultivar name 'Caramel'.

The inventor discovered the new cultivar, 'Caramel' as a chance seedling in a cultivated nursery bed in Hantay, France, CT in 2003. Although the parentage is unknown, the characteristics of the new cultivar and the proximity of plants of *Heuchera villosa* 'Autumn Pride' (not patented) suggests that 'Autumn Pride' is a probable parent.

The new cultivar was selected for its unique foliage that emerges grey-red in color and matures to a golden yellow-green color. The foliage color of 'Autumn Pride' is green. 'Caramel' is most similar in foliage coloration to *Heuchera* 'Amber Waves' (U.S. Plant Pat. No. 13,348), a *Heuchera* of hybrid origin. 'Caramel' differs in having foliage that is less ruffled, more cordate in shape, and more sunfast.

Asexual reproduction of the new cultivar was first accomplished under direction by the inventor by in vitro propagation in The Netherlands in the fall of 2003. Asexual reproduction of the new cultivar by division and tissue culture has shown that the unique features of 'Caramel' are stable and reproduced true to type in successive generations.

SUMMARY OF THE INVENTION

The following traits have been repeatedly observed and represent the characteristics of the new cultivar. These attributes in combination distinguish 'Caramel' as a new and unique cultivar of *Heuchera.*

1. 'Caramel' has foliage with the unique coloration of emerging greyed-orange and turning to a golden yellow-green on maturity.
2. The leaves of 'Caramel' are cordate in shape and fairly flat in aspect.
3. 'Caramel' reaches a plant height of 60 cm in bloom.

4. 'Caramel' is vigorous grower compared to the growth rate that is typical for *Heuchera* with colored foliage and has been shown to be resistant to diseases under the conditions tested.

BRIEF DESCRIPTION OF THE DRAWING

The accompanying colored photographs illustrate the overall appearance and distinct characteristics of the new *Heuchera*. The photographs were taken in The Netherlands in April of a one year-old plant grown outdoors in a field plot.

The photograph on the first sheet provides an overall view of foliage characteristics of new cultivar.

The photographs on the second sheet are close-up views of the foliage of 'Caramel'; the top photo provides a view of the foliage as it emerges and changes with maturity (clockwise) and the bottom photograph is of a mature leaf. The colors in the photographs are as close as possible with the photographic and printing technology utilized. The color values cited in the detailed botanical description accurately describe the colors of the new *Heuchera.*

DETAILED BOTANICAL DESCRIPTION OF THE PLANT

The following is a detailed description of a one year-old plant of the new cultivar as grown outdoors in The Netherlands. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Caramel' is a cultivar of *Heuchera villosa.*

Parentage: Chance seedling, most probably a seedling of *Heuchera villosa* 'Autumn Pride'.

General description:

*Plant habit*.—Clump-forming herbaceous perennial, mounded foliage.

*Height and spread*.—Reaches about 60 cm in height in bloom and about 28 cm in width. Foliage reaches a height of about 12 cm.

*Hardiness*.—Cold hard to at least USDA Zone 6.

*Culture*.—Full sun to medium shade in moist, well-drained, fertile soils.

*Diseases and pests*.—Disease free in the conditions tested, no susceptibility or resistance to pests has been observed.

*Root description*.—Fibrous roots on woody rootstalks.

*Branching habit*.—Basal rosettes of leaves on petioles.

*Propagation*.—In vitro propagation is the preferred method, division are also possible.

*Root initiation*.—Roots appear in rooting media in 10 day at 20° C. in the laboratory without supplemental lighting.

*Root development*.—Rooted transplants from tissue culture fully develop in a 2.5 in container in about 20 days in a greenhouse with average temperatures of about 20° C. without supplemental lighting in The Netherlands.

*Growth rate*.—Vigorous compared to what is typically observed for *Heuchera* with colored foliage. A 2.5 inch container will fully develop in a one-gallon container in 2 to 2.5 months in the Netherlands.

Foliage description:

*Leaf shape*.—Cordate.

*Leaf division*.—Simple, but lobed with about 7 lobes per leaf.

*Leaf base*.—Strongly cordate (leaves at base overlap).

*Leaf apex*.—Acute to rounded.

*Leaf venation*.—Palmate, conspicuous but not prominent, vein color on upper surface of mature leaves 152D, vein color on lower surface of mature leaves N170D.

*Leaf margins*.—Crenate, average of 2.5 teeth per cm.

*Leaf attachment*.—Petiolate.

*Leaf arrangement*.—Basal rosettes.

*Leaf orientation*.—Held horizontal to petiole, held nearly flat (not ruffled or curled).

*Leaf surface*.—Upper: pubescent with 1 mm stiff white hairs, lower: glabrous with pubescence on veins.

*Leaf color*.—Young leaves (upper surface): greyed-orange 176A with margin area 177B. Young leaves (lower surface): greyed-red to greyed-purple ranges from 178A to 183C. Mature leaves (upper surface): yellow-green 152A to 152B (color slightly more brownish as if overlaid with 199A). Mature leaves (lower surface): greyed-red 182B to 182C.

*Leaf size*.—About 8 cm in length, up to about 7.7 cm in width.

*Leaf quantity*.—About 11 per basal rosette.

*Petiole size*.—Up to about 9 cm in length, about 2 mm in width.

*Petiole color*.—182C.

*Petiole shape*.—Round.

*Stipules*.—2 leafy stipules at the base of each petiole, oblong in shape, 1 cm in length, 2 mm in width, color 182C (both surfaces), margins sparsely covered with short hairs.

Flower and seed description: Flowering has not been observed on the plants under the conditions tested.

It is claimed:

1. A new and distinct cultivar of *Heuchera* plant named 'Caramel' as herein illustrated and described.

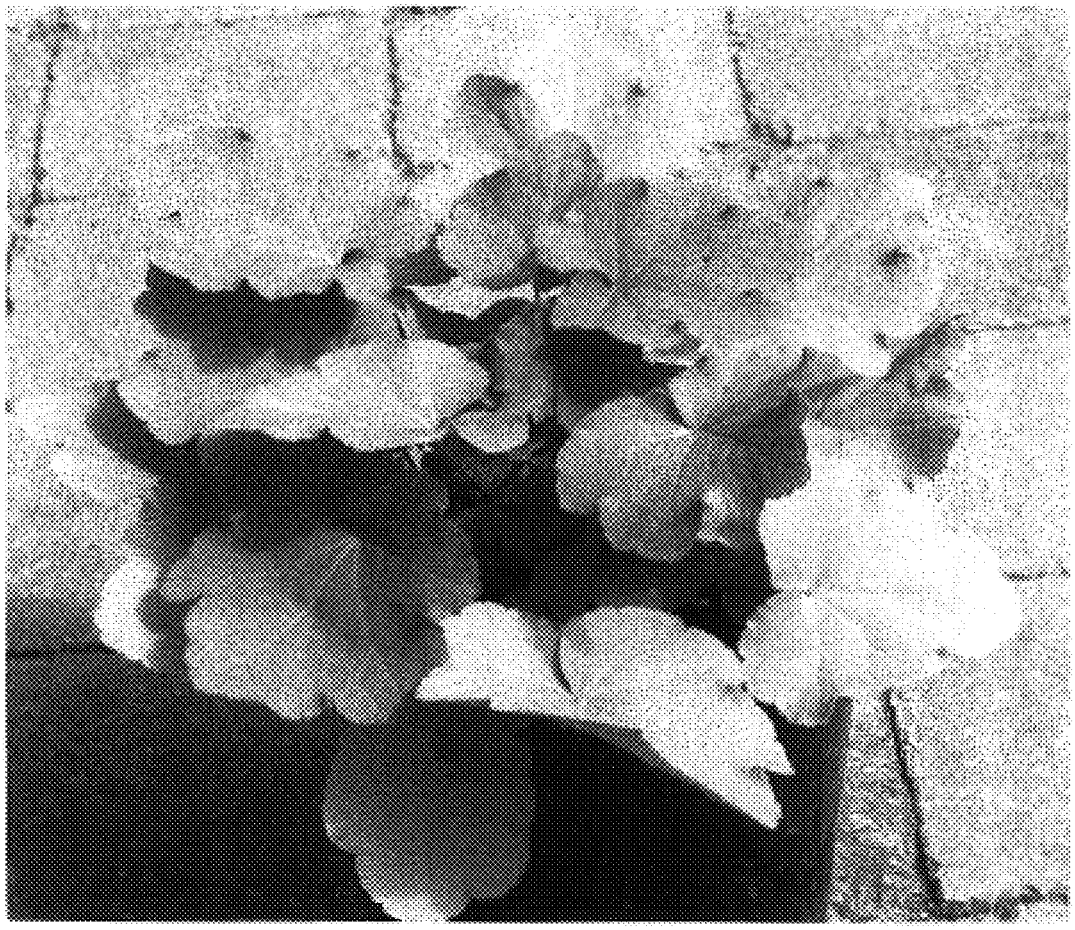

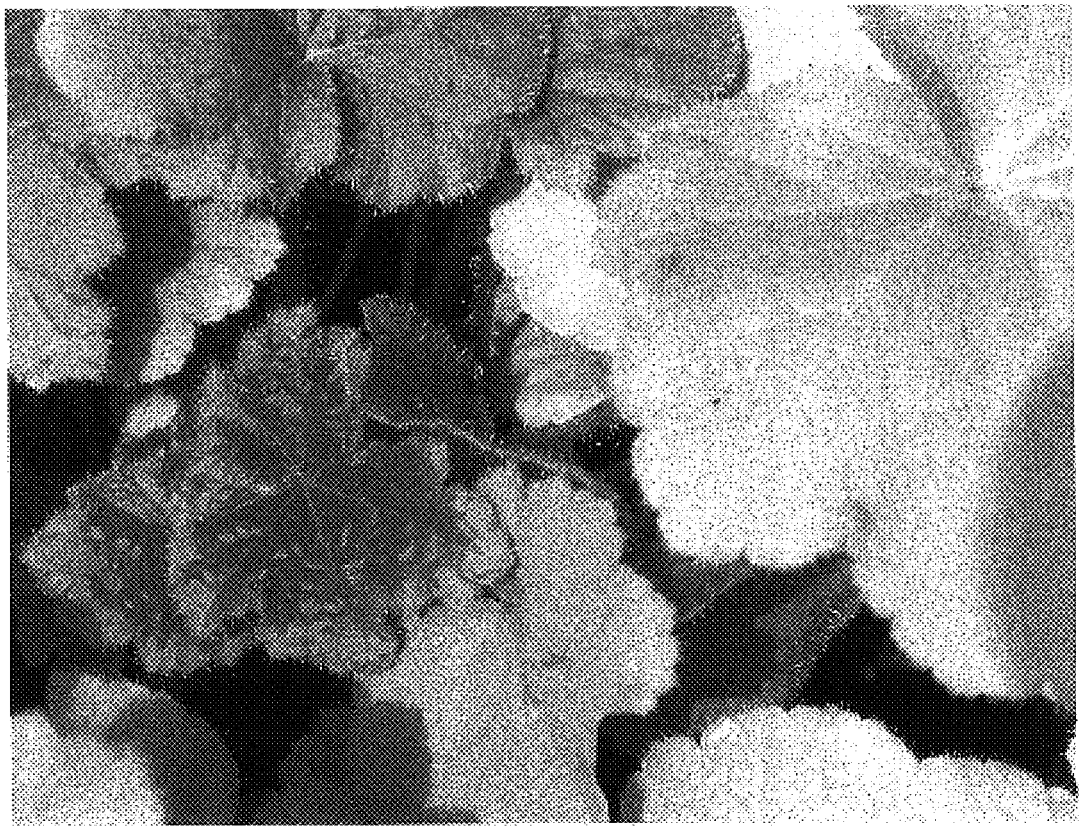
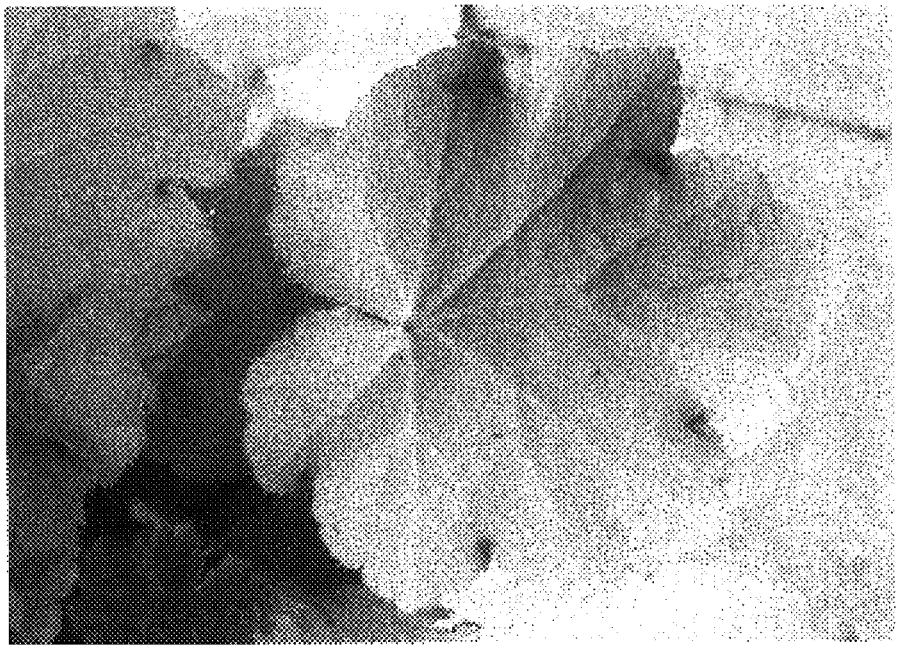

* * * * *